(12) United States Patent
Xie et al.

(10) Patent No.: US 8,574,633 B2
(45) Date of Patent: Nov. 5, 2013

(54) HUPERZIA SERRATA (THUNB.) TREV. COMPOSITION COMPRISING COMPOUNDED HUPERZINE A AND HUPERZINE B AND METHODS FOR PREPARING IT

(75) Inventors: Delong Xie, Shanghai (CN); Jiajun Xie, Shanghai (CN); Jun Wang, Shanghai (CN); Xinsheng Huang, Shanghai (CN)

(73) Assignees: Delong Xie, Shanghai (CN); Jiajun Xie, Shanghai (CN); Jun Wang, Shanghai (CN)

( * ) Notice: Subject to any disclaimer, the term of this patent is extended or adjusted under 35 U.S.C. 154(b) by 406 days.

(21) Appl. No.: 11/754,029

(22) Filed: May 25, 2007

(65) Prior Publication Data

US 2007/0286911 A1 Dec. 13, 2007

Related U.S. Application Data

(63) Continuation of application No. PCT/CN2005/001992, filed on Nov. 24, 2005.

(30) Foreign Application Priority Data

Nov. 26, 2004 (CN) .......................... 2004 1 0084633

(51) Int. Cl.
*A61K 36/00* (2006.01)
(52) U.S. Cl.
USPC ........................................................ 424/725
(58) Field of Classification Search
None
See application file for complete search history.

(56) References Cited

U.S. PATENT DOCUMENTS 5,177,082 A * 1/1993 Yu et al. .................. 514/286

FOREIGN PATENT DOCUMENTS

| CN | 1047732 | | 12/1999 |
|---|---|---|---|
| CN | 1279065 | A | 10/2001 |
| CN | 1383824 | A | 12/2002 |
| CN | 1101381 | | 2/2003 |
| CN | 1448390 | A | 10/2003 |
| CN | 1450882 | A | 10/2003 |
| WO | WO 02085341 | A2 * | 10/2002 |

OTHER PUBLICATIONS

Lishizen Medicine & Materia Medica Res., vol. 13, No. 13, pp. 176-179, 2002, Abstract.
Office Action issued by the State Intellectual Property Office of China in Application No. CN2005800470129 on Feb. 27, 2009.
Yu Weijian, et al. "HPLC Determination of Huperzine A and Its Preparation." Chinese Journal of Pharmaceuticals, 30(8), 1999, pp. 363-364.
Zha Shenghua, et al. "Microwave-assisted Extraction of Huperzine A and Huperzine B from *Huperzia serratum*." China Biothechnotogy, 24(11), 2004, pp. 23-24.
Dictionary of Traditional Chinese Medicine, 215, Medical College of Zhejiang, 1977 (with English language translation).

* cited by examiner

*Primary Examiner* — Amy L Clark
(74) *Attorney, Agent, or Firm* — Hamre, Schumann, Mueller & Larson, P.C.

(57) ABSTRACT

The invention is directed to the field of natural medicine, specifically to alkaloid extracts of *Huperzia serrata* (Thunb.) Trev. A *Huperzia serrata* (Thunb.) Trev. composition and the method for preparing it are provided. The *Huperzia serrata* (Thunb.) Trev. composition comprises Huperzine A and Huperzine B, wherein the total content of the said Huperzine A and Huperzine B is 50-99 wt % of total alkaloids and the weight ratio of the said Huperzine A and Huperzine B is 1:0.5-5. The *Huperzia serrata* (Thunb.) Trev. composition of the invention has good therapeutic effect and improved safety.

7 Claims, No Drawings

HUPERZIA SERRATA (THUNB.) TREV. COMPOSITION COMPRISING COMPOUNDED HUPERZINE A AND HUPERZINE B AND METHODS FOR PREPARING IT

CROSS-REFERENCE TO RELATED APPLICATIONS

This application is a continuation of International application number PCT/CN2005/001992, filed Nov. 24, 2005 which claims priority to Chinese application No. CN 200410084633.1 filed Nov. 26, 2004, the contents of both are herein incorporated in their entirety by reference.

FIELD OF THE INVENTION

The invention is directed to the field of natural medicament, specifically, alkaloid extracts of *Huperzia serrata* (Thunb.) Trev. (which is also referred as "*Huperzia serrata* (Thunb.) Trev. Composition") comprising Huperzine A and Huperzine B and the use thereof.

BACKGROUND ARTS

Along with the protracting of the natural life, the incidence of central psychogenic diseases of studying memory and cognition dysfunction, such as infant intelligence development retardation, adult dysmnesia, and Alzheimer's disease, are increasing. The last one is especially becoming a social problem and arousing people's high attention.

Alzheimer's disease (AD) is also called senile dementia or presenile dementia. It is a kind of lethal central nervous system retrogressive disease mainly represented as progressive cognition dysfunction and memory loss. According to the latest estimation of WHO (World Health Organization), the invasion population of AD in the world now is more than 20 million. The number of the population of AD is 10% of the crowd of more than 65 years old, and is 50% of the crowd of more than 85 years old. In US, 4 million people had meek cognition trauma, another 4 million people had AD, and the sick population is dramatically increasing. In China, the population of AD is creasing gradually along with the aging society. According to the result of AD epidemiological primary survey done by Peking Union Medical College Hospital, it showed AD disease incidence is 4.2% among the people of 65 years old or more in north China. Therefore, predictably there are about 5 million AD patients in China based on that at present there are 1.3 hundred million people who are more than 60 years old in China.

The cause of AD is still not recognized clearly till now, but various basic and clinical studies proved that the memory lesion and progressive cognition dysfunction of AD is closely related to the persistent relative deficiency of acetylcholine, which is the transmitter in central nervous system. The pathophysiological research showed a lot neurons in AD patients' cerebrum were lost, together with the decrease of the concentration of various neurotransmitters in central nervous system, especially the decrease of acetycholine. The lost neurons are those in neocortex, hippocampal, basal nuclei and locus ceruleus etc. of cerebrum. The distinct hypofunction of central acetylcholine system is a main pathologic change of AD anticipation, which is also present in the whole course of the disease. Using cholinomimetic including cholinoprodrug, cholinesterase inhibitor (AchEI), selective M, N choline receptor agonist had obvious therapeutic effect on delaying the occurrence and development of AD, alleviating the memory and cognition dysfunctions.

Tacrine is the first AchEI approved by FDA for treating AD. Although it is effective, it is strictly restricted clinically because of its high liver toxicity. Both tacrine and E2020, which is approved by FDA in 1996, were called first generation AchEI.

Comparing with the first generation AchEI, the medicament only with Huperzine A as its active ingredient (the trade name is Haperzine, or Selagine) belonged to the second generation AchEI, which had high selectivity with AchE in brain and had higher safety.

The clinical trials showed that the period of administration to prevent and treat the memory and cognition dysfunction was relatively long. It would last the whole life for the patients of AD. Under the circumstance, the safety of the medicament is the most important.

So it is imminently needed a kind of medicament in the field, which has good therapeutic effect and meanwhile is more safe.

SUMMARY OF THE INVENTION

An objective of the invention is to provide a *Huperzia serrata* (Thunb.) Trev. composition comprising Huperzine A (HupA) and Huperzine B (HupB). The other objective of the invention is to provide a method for preparation of the composition.

In first aspect of the invention, it provided a *Huperzia serrata* (Thunb.) Trev. composition, wherein the content of total alkaloids is 30-99 wt %, the said total alkaloids comprised Huperzine A and Huperzine B, the total content of the said Huperzine A and Huperzine B is 50-99 wt % of total alkaloids, most preferred is 50-90 wt %.

In the above mentioned *Huperzia serrata* (Thunb.) Trev. compositions, the weight ratio of the said Huperzine A and Huperzine B is 1:0.5-5. In another preferred embodiment, the weight ratio of Huperzine A and Huperzine B is 1:0.7-5; more preferred 1:0.8-3; and the most preferred 1:1-2.5.

In addition to Huperzine A and Huperzine B, the above mentioned composition also comprised one or more member selected from Huperzine C, Huperzine D, Huperzine E, Huperzine F, Huperzine G, 6-β-hydroxyhuperzine A, Huperzinine, Lycodoline, Lycodavine, Serratinine, Serratine, 8-Deoxyserratinine, and Phlegmariurine N.

In addition to total alkaloids, the above mentioned composition comprised one or more selected from Galangin, Kaempferol, Quercetin, Apigenin, Genkwanin, Luteolin, Vitexin, Serratenediol, Serratriol, Tohogenol, and 21-epi-Serratenediol, wherein the thereof is 1-50 wt % of the total weight of the composition.

In the second respect of the invention, it provided a method for preparing the above-mentioned *Huperzia serrata* (Thunb.) Trev. composition. The method comprised the steps of:

a. Extracting the crude preparation of *Huperzia serrata* (Thunb.) Trev. with acid aqueous solution of pH 1-3 to obtain the extract solution of the crude preparation; extracting the residue with aqueous solution to obtain the extract solution of the residue;

b. Concentrating the extract solution of the crude preparation and the extract solution of the residue respectively and processing the thus obtained concentrates as follows:

(b1) extracting, concentrating, decolorizing and reconcentrating the extract of the crude preparation to get the reconcentrate, adding to a chromatography column, eluting with water, C1-C6alkanol solvent, or the mixed solution of water and C1-C6 alkoxide solvent to collect fraction b1 containing total alkaloids;

(b2) Diluting, and centrifuging the extract of the residue to get centrifugate, adding the centrifugate to chromatography column and eluting the centrifugate with water, polar solvent, nonpolar solvent, or the mixed solution of water and these solvents to collect fraction b2 containing total alkaloids;

c. Combining fractions b1 and b2, concentrating and drying to obtain the *Huperzia serrata* (Thunb.) Trev. composition.

The acid aqueous solution in step a is selected from: hydrochloric acid, tartaric acid or citric acid; the said aqueous solution to extract the extract of the residue in step a containing alcohol is selected from methanol and ethanol.

In another preferred embodiment, the said C1-C6 alkanol solvent in step b1 is selected from: methanol, ethanol, n-butanol, C-4 alkanol, C-5 alkanol, or the mixture thereof with water of any proportion; the said a polar solvent in step b2 is selected from methanol or ethanol.

In another preferred embodiment, in step a, pulverize the crude preparation of *Huperzia serrata* (Thunb.) Trev. in the extracting tank and add 10-20 fold of aqueous solution comprising inorganic acid or organic acid. Stir dynamically to obtain the extract of the crude preparation. The residues are extracted through reflux with water or aqueous ethanol solution. More preferably, the inorganic acid or organic acid used to extract the crude preparation is selected from hydrochloric acid and tartaric acid of 0.5-1.5%. Stirring dynamically, the temperature of extraction is 20-50° C., and the time of extraction is 6-48 hours. The concentration of ethanol in the ethanol water solution used for extracting the residues is 20-95%, the temperature of reflux is 80-100° C., and the duration is 1-3 hours.

In another preferred embodiment, concentrating the extract solution of the crude preparation and the extract solution of the residue respectively to get the concentrations, which is no more than 10-15% of the original wt/v.

In another preferred embodiment, extract the concentrate of the crude preparation with chloroform, concentrating to remove chloroform, decolorize with activated carbon after extracting with acid in water.

In another preferred embodiment, adjusting the pH value of the concentrate of the crude preparation obtained by step b to 8-10 with aqueous ammonia and extracting with chloroform 3-6 times repetitively. Combining the chloroform extracts and concentrating to remove chloroform. The concentrate is no more than 10% of the original wt/v. Extracting the above mentioned concentrates with 1%-4% citric acid or hydrochloric acid in water 1-3 times repetitively. Diluting the extract extracted with acid water solution 10 times and adding activated carbon, whose volume is 1 %-2% of the diluted solution. Stirring for 10-30mins and filtering to get transparent solution. Concentrating the above solution to the volume of no more than 10% of the original one.

In another preferred embodiment, the chromography column used in steps b1 and b2 is silicon gel column, or macroporous resin or cation exchange resin or polyamide resin; the eluting solution used is C1-C3 alkanol solvent, acetone, chloroform, or methyl ester or ethyl ester of C1-C3 alkanol.

In another preferred embodiment, gradient elution is used in steps b1 and b2.

In another preferred embodiment, adding 2-4 folds deionized water to the residues extract obtained in step b1, stirring homogenously and precipitating for 6 hours. Centrifuging the supernatants with high speed of 16000 r/min. Loading centrifugate onto the chromatography column of macroporous resin or cation exchange resin or polyamide resin and eluting gradiently with water, C1-C3 alkanol solvent or the arbitrary proportion mixture solution of them. Collecting the high content fractions.

In another preferred embodiment, combining and concentrating the fractions obtained in steps b1 and b2 to 10-20% of the original volume. lyophilize, spray dry or vacuum dry.

In the third aspect of the invention, it provides use of the *Huperzia serrata* (Thunb.) Trev. composition for the manufacturing of a medicament which reduces the undesired effects of Huperzine A.

In the forth aspect of the invention, it provides use of the *Huperzia serrata* (Thunb.) Trev. composition for the manufacturing of the pharmaceutical composition, food composition or diet supplement which enhances memory function in children, ameliorate dysmnesia in adult, or prevent or treat Alzheimer's disease.

In another preferred embodiment, the said pharmaceutical composition comprises the *Huperzia serrata* (Thunb.) Trev. composition and the pharmaceutical acceptable carriers. The said pharmaceutical acceptable carriers include starch, dextrin, gelatin, saccharide, sugar alcohol, methylcellulose, carboxyl methyl cellulose, carboxyl ethyl cellulose, polyvinyl alcohol, polyacrylic acid or the derivatives thereof, stearate or one or more of magnesium salts or calcium salts.

In another preferred embodiment, the said pharmaceutical composition includes oral administration, injection, transdermal administration or mucosa drug delivery medicament.

In another preferred embodiment, the medicament is tablet, capsule, granule, nasal, aerosol, powder for injection or PAP Patcher.

In the fifth aspect of the invention, it provides use of Huperzine B for the manufacturing of a medicament which reduces the side effects of Huperzine A.

In another preferred embodiment, the said medicament, which reduces the side effects of Huperzine A, comprises Huperzine A and Huperzine B and the weight ratio of the said Huperzine A and Huperzine B is 1:0.5-5.

The *Huperzia serrata* (Thunb.) Trev. composition and the method for preparing it mentioned in the invention provide a composition not only therapeutically beneficial but also highly safe.

DETAILED DESCRIPTION OF THE INVENTION

Through extensive and intensive study, the inventors unexpectedly discovered the extract of *Huperzia serrata* (Thunb.) Trev. comprising both HupA and HupB having not only the high efficacy of HupA as a reversible cholinesterase activity inhibitor but also the apparently improved safety than using HupA alone.

*Huperzia serrata* (Thunb.) Trev. is also called Herba Lycopodii Serrati. It is recorded as a medicinal plant in "Ben Cao Shi Yi" authored by Chen Zangqi in Tang Dynasty and in "zhi Wu Ming Shi Tu Kao" authored by Wu Qijun in Qing Dynasty of China. Chinese people use it to treat traumatic injuries, snake-bite and burns. It is reported that Huperzia serrata (Thunb.) Trev. is affective in reducing a fever, dehumidifying, removing bruise, and hemostasis, etc., and it is used to treat pneumonia, pulmonary abscess, over-strained hemoptysis, hemorrhoids, leucorrhagia, traumatic injuries, and toxic swelling etc. In 1972, the researchers from China for the first time found that the alkaloid extracted from the plant had the activity of relaxing animal's striated muscle. In 1980, the researchers further separated the alkaloid Huperzine A from the plant, which had strong bioactivity. HupA belongs to reversible cholinesterase inhibitors, which can penetrate blood-brain barrier. HupA has apparent effects of improving the memory recovery and memory protection, enhancing normal people's memory and cognition function, improving memory dysfunction in adult, and reducing the ongoing cognition dysfunction and memory injury of AD patients. However, administration of Hup A alone induces severe side effects, including nausea, anorexia, dizziness, xerostomia and seizure susceptibility, etc.

The total alkaloids in the invention refers to the total alkaloids extracted from *Huperzia serrata* (Thunb.) Trev., wherein in addition to HupA and HupB, it also includes one or more of HupC, HupD, HupE, HupF, HupG, 6-β-hydroxyl Huperzine A, Huperzinine, Lycodoline, Lycodavine, Serratinine, Serratine, 8-Deoxyserratinine, and Phlegmariurine N.

High Performance Liquid Chromatography (HPLC) could be used for isolation and quantitatively assay for the contents of HupA, HupB, HupC, HupD, HupE. The bed is octadecyl silane linked silicon gel, the mobile phase is acetonitrile: triethylamine phosphate buffer (85:15), the detecting wave length is 308 nm, and the resolution is more than 1.5.

As used in the invention, the term "*Huperzia serrata* (Thunb.) Trev. composition" and "the extract of *Huperzia serrata* (Thunb.) Trev." can be used exchangeably. Both indicate *Huperzia serrata* (Thunb.) Trev. composition wherein the content of total alkaloids is 30-99 wt %, the said total alkaloids comprises Huperzine A and Huperzine B, and the weight ratio of the said Huperzine A Huperzine and B is 1:0.5-5; preferably 1:0.7-5, more preferably 1:0.8-3, most preferably 1:1-2.5. The total content of the said Huperzine A and Huperzine B in the *Huperzia serrata* (Thunb.) Trev. composition is 50-99 wt % of total alkaloids;. more preferably 50-90%.

In addition to the total alkaloids in the *Huperzia serrata* (Thunb.) Trev. composition of the invention, it also comprises one or more of Galangin, Kaempferol, Quercetin, Apigenin, Genkwanin, Luteolin, Vitexin, Serratenediol, Serratriol, Tohogenol, and 21-epi-Serratenediol. The total content is 1-50 wt % of the weight of the composition.

The invention also provides the pharmaceutical composition, food composition or diet supplement, which comprises *Huperzia serrata* (Thunb.) Trev. composition or the extract of *Huperzia serrata* (Thunb.) Trev. It comprises safe and effective amount of *Huperzia serrata* (Thunb.) Trev. composition or the extract of *Huperzia serrata* (Thunb.) Trev. (i.g. 0.5-99%, preferably 1-80%, more preferably 2-60%) and the pharmaceutically or food acceptable carriers, wherein the weight ratio of Huperzine A and Huperzine B is 1:0.5-5.

As used in the invention, the term "essential components" means the essential chemical substances as active components, i.e. HupA and HupB.

As used in the invention, the term "substantially comprising" means that in addition to the essential components in the composition, it also comprises few less important components and/or impurities which do not affect the effective components. For example, it can comprise the sweetener to improve the flavor, antioxidant to prevent oxidation, Chinese traditional medicines or their extract or their active content to increase the clinical effect and safety, vitamins or amino acids or the mineral substances or the minor elements to improve the therapeutic effectiveness and the health condition of human body, and other commonly used additives in the art.

As used herein, the term "pharmaceutically acceptable carrier" refers to a carrier for administration of a therapeutic agent and includes various excipients and diluents. The term refers to any pharmaceutical carrier which is not a necessary active ingredient and which may be administered without undue toxicity. Suitable carriers are well known to those of ordinary skill in the art. A thorough discussion of pharmaceutically acceptable excipients is available in Remington's Pharmaceutical Sciences (Mack Pub. Co., N.J. 1991). Pharmaceutically acceptable carriers in the compositions may contain liquids such as water, saline, glycerol and ethanol. Additionally, auxiliary substances, such as wetting or emulsifying agents, pH buffering substances, and the like, may be present in such vehicles. In addition to the essential components of *Huperzia serrata* (Thunb.) Trev. (such as HupA and HupB), the unnecessary components from *Huperzia serrata* (Thunb.) Trev. and other unnecessary components e.g. other supplemental herbs) are also in the scope of this term.

For example, the composition of the invention can also comprise, but not limited to the following Chinese traditional medicines or their extract or their active content: ginseng, acanthopanax root, gingko nut, fiveleaf gynostemma, pueraria root, Rhizoma Anemarrhenae, red sage root, astragalus root, Herba Hyperici Erecti, fleabane, Chinese angelica root, eucommia bark, gastrodia tuber, green tea, safflower and their extract or their active content, and the mixture of their extract and their active content.

For example, the composition of the invention can also comprise but not limited to the following water-soluble vitamins and lipid-soluble vitamins: Vitamin A, Vitamin B1, B2, B3, B4, B5, B6, B12, B15, B17, Vitamin C, Vitamin D, Vitamin E, Vitamin K, Vitamin P, choloic acid, folic acid, inositol, biotin, and the mixture of the above mentioned vitamins.

For example, the composition of the invention can also comprise, but not limit to, the following amino acids: alanine, arginine, glycine, histidine, lysine, methionine, ornithine, phenylalanine, tyrosine, valine, N-acetylcysteine, γ-propalanine, carnic acid, and the mixture of the above mentioned amino acids.

For example, the composition of the invention can also comprise, but not limit to, the following mineral substances or microelements: calcium, iron, phosphorus, potassium, magnesium, zinc, chromium and the mixture of the above mentioned mineral substances or microelements.

The invention provides a method for obtaining the above mentioned *Huperzia serrata* (Thunb.) Trev. composition, comprising the steps of:

a. Extracting the crude preparation of *Huperzia serrata* (Thunb.) Trev. with acid aqueous solution of pH 1-3 to obtain the extract solution of the crude preparation; extracting the residue with aqueous solution to obtain the extract solution of the residue;

b. Concentrating the extract solution of the crude preparation and the extract solution of the residue respectively and processing the thus obtained concentrations as follows:

(b1) extracting, concentrating, decolorizing and reconcentrating the extract of the crude preparation to get the reconcentrate, adding to a chromatography column, eluting with water, C1-C6alkanol solvent, or the mixed solution of water and C1-C6 alkoxide solvent to collect fraction b1 containing total alkaloids;

(b2) Diluting, and centrifuging the extract of the residue to get centrifugate, adding the centrifugate to chromatography column and eluting the centrifugate with water, polar solvent, nonpolar solvent, or the mixed solution of water and these solvents to collect fraction b2 containing total alkaloids;

c. Combining fractions b1 and b2, concentrating and drying to obtain the *Huperzia serrata* (Thunb.) Trev. composition.

The pharmaceutical composition or the diet supplement can be prepared into common medicament by common methods. The preferred were tablet, capsule, granule, nasal, aerosol, powder for injection or PAP Patcher.

The composition of the invention could be commonly administered, for example by oral administration. When administering, the dosage is usually at least 0.5 µg/kg body weight one day calculated by the total weight of HupA and HupB. In most cases no more than 300 µg/kg body weight, preferably the dosage is 1-50 µg/kg body weight. Based on HupB, the dosage is 1-40 µg/kg body weight per day. Of course the specific dosage is decided by the administration routes and the health condition of the patient, which is within the capability of the skilled physicians.

The main advantages of the invention include:
1. Exerting the beneficial effect as a reversible inhibitor of cholinesterase of HupA, and substantially improving the safety compared with using HupA alone;
2. Effectively exerting HupB, which is the waste substance in the art;
3. Apparently reducing the cost.

The invention is further illustrated by the following examples. These examples are only intended to illustrate the invention, but not to limit the scope of the invention. For the experimental methods in the following examples, they are performed under routine conditions, or as instructed by the manufacturers, unless otherwise specified.

The assay methods of the invention are listed as following:

HPLC Assay for the Contents of HupA and HupB

Chromatography condition and system adaptability test: using octadecyl silane linked silicon gel as loading material; the mobile phase is 0.02 mol/L monopotassium phosphate (pH4.5)-acetonitrile (88:12); the assay wave length is 308 nm. The theoretical plate number calculated by the peak of HupA is not less than 2000; the resolution of HupA and HupB is more than 1.5.

Preparation of the control solution: weighing the control of HupA and HupB precisely and dissolving them with hydrochloric acid to make a control solution containing 10 µg/ml HupA and HupB respectively.

Preparation of the test solution: weighing the proper weight of the extract of *Huperzia serrata* (Thunb.) Trev. precisely and dissolving it with hydrochloric acid to make a solution containing 100 ug of the extract of *Huperzia serrata* (Thunb.) Trev. per 1 ml. Shaking the solution homogeneously, filtering it and throwing away the primary filtrate and obtain the filtrate as the test solution.

Assay: Precisely aspirate 10 µl of the control solution and the test solution respectively, and injecting them into the liquid chromatograph, calculating the content of HupA and HupB of the sample by external standard method.

Content Assay of Total Alkaloids of *Huperzia serrata* (Thunb.) Trev. -Acid Base Titration Assay: Precisely weighing 1 mg of the *Huperzia serrata* (Thunb.) Trev., adding 0.5 ml sodium hydroxide of 1 mol/l, putting it in the separating funnel, extracting 4 times with chloroform of 10 ml, 10 ml, 5 ml, 5 ml respectively, combining the chloroform extract solutions and putting in an Erlenmeyer flask with a plug, adding titration solution of 0.01 mol/l sulfuric acid precisely and 10 ml of the cold newly boiled water, shaking completely and adding 1-2 drops of indictor of sodium alizarin sulfonate, titrating with 0.02 mol/l titrating solution of sodium hydroxide to weak yellow, and correcting the titration result with the blank.

Content Assay of HupA, HupB, HupC, HupD, HupE-HPLC

Chromatography condition and system adaptability test: using octadecyl silicon hydride linked silicon gel as loading material; the mobile phase is acetonitrile: triethylamine phosphate (85:15); the assay wave length is 305 nm. The theoretical plate number calculated by the peak of HupA is not less than 2000.

Preparation of the control solution: weighting the proper weight of the controls of HupA, HupB, HupC, HupD, and HupE precisely ,dissolving them respectively with 0.01 mol/l hydrochloric acid solution. Diluting quantitatively to formulate the control solution containing 10 ug per 1 ml.

Preparation of the test solution: weighting the proper weight of the extract of *Huperzia serrata* (Thunb.) Trev. precisely and dissolving with hydrochloric acid. Diluting it quantitatively to formulate the solution containing 10 µg per 1 ml. Shaking the solution homogeneously, filtering and discarding the primary filtrate to obtain the test solution. Weighting the proper weight of the tested sample precisely and dissolving it with 0.01 mol/l hydrochloric acid solution to obtain a test solution containing 40 µg per ml.

Assay: Precisely absorbing 20 ul of the control solution, and injecting into the liquid chromatograph to record the chromatogram. Weighting the proper weight of the control sample of HupA, HupB, HupC, HupD, and HupE and assay as before. Calculating the content of the sample according to the peak area by the external standard method.

Content Assay of Total Alkaloids-Spectrophotometry

Preparation of the control solution: Precisely weighting the 20 mg rutin control, which is dried under reduced pressure at 120° C. to constant weight, and put it in the 100 ml volumetric flask. Adding 70 ml 70% ehtanol and heating slightly on the water bath to make it dissolve. Cooling and diluting to graduation with ethanol. Shaking homogeneously to get the control solution (0.2 mg anhydrous rutin per ml).

Preparation of the standard curve: Precisely absorbing 0.2, 0.4, 0.6, 0.8, 1.0, 1.2 ml of the control solution and putting them in a volumetric flask of 10 ml respectively. Respectively adding 3 ml water, 2 ml buffer solution of acetic acid-sodium acetate with pH4.5, and 2 ml aluminum chloride solution of 0.1 mol/l. Shaking homogeneously, adding 70% ethanol to graduation and Shaking homogeneously again. Using corresponding solvent as the blank, determining the absorbance at the wave length of 270 nm. raffing the standard curve with concentration to absorbance.

Assay: Weighting 25 mg the extract of *Huperzia serrata* (Thunb.) Trev. and drying at 50° C. under reduced pressure for 2 hours. Precisely weighting dried extract of *Huperzia serrata* (Thunb.) Trev. and putting it into a 50 ml volumetric flask. Adding 70% ethanol to graduation and Shaking homogeneously. Absorbing 0.5 ml precisely and putting it into a 10 ml volumetric flask. Following the method under the item of the preparation of the standard curve, assaying the absorbance from "added 3 ml water". Read out the weight of the total alkaloids (mg) of the test solution, which is equal to that of rutin, on the standard curve and calculated.

EXAMPLE 1

Preparation Procedure I:
Abstracting: pulverize 100 kg *Huperzia serrata* (Thunb.) Trev. in the extracting tank and put in 20 fold water solution containing 1.5% tartaric acid. Stir dynamically to abstract for 36 hours under the condition of 30° C.;

Concentrating: Concentrate the solution from permeation to 100 L;

Extracting: Adjust the pH value of the enriched solution to 8.5 with aqueous ammonia and extract with chloroform 4 times repetitively. Combine the chloroform extraction solution and concentrate to remove chloroform. Concentrate to 100 L;

Back extraction with acid: Extract the above mentioned solution with 2% citric acid water solution 3 times repetitively;

Activated carbon decolorizing: Dilute the extraction solution of acid water 10 fold. The add-on of the activated carbon is 1% of the volume of the diluted solution. Stir 30 minutes and filter to get transparent solution;

Concentrating: Concentrate the above mentioned solution to 200 L;

Column chromatography: Load the above mentioned extractum onto the silicon gel column and elute gradiently with the eluent of methanol-chloroform. Collect the fractions of the eluent of methanol-chloroform (85:15);

Concentrate the above combined fractions to 200 ml and lyophlize in vacuum refrigeration machine to obtain 12 g of the extract of *Huperzia serrata* (Thunb.) Trev. The yield of the extract was 0.012% by the herb, containing 66% HupA and 33% HupB.

EXAMPLE 2

Preparation Procedure II:

Abstracting: pulverize 100 kg *Huperzia serrata* (Thunb.) Trev. in the extracting tank and put in 20 fold water solution containing 1.5% tartaric acid. Stir dynamically to abstract for 36 hours under the condition of 45° C.;

Concentrating: Concentrate the solution from permeation to 100 L;

Extracting: Adjust the pH value of the enriched solution to 9 with aqueous ammonia and extract with chloroform 4 times repetitively. Combine the chloroform extraction solution and concentrate to remove chloroform. concentrate to 100 L;

Back extraction with acid: Extract the above mentioned solution with 2% citric acid water solution 3 times repetitively;

Activated carbon decolorizing: Dilute the extraction solution of acid water 10 fold. The add-on of the activated carbon is 1% of the volume of the diluted solution. Stir 30 minutes and filter to get transparent solution;

Concentrating: Concentrate the above mentioned solution to 200 L;

Column chromatography: Load the above mentioned extractum onto the silicon gel column and elute gradiently with the eluent of methanol-chloroform. Collect the fractions of the eluent of methanol-chloroform (50:50);

Concentrate the above combined fractions to 500 ml and lyophlize in vacuum refrigeration machine to obtain 30 g of the extract of *Huperzia serrata* (Thunb.) Trev. The yield of the extract was 0.03% by the herb, containing 52% HupA and 39% HupB.

EXAMPLE 3

Preparation Procedure III:

Abstracting: pulverize 100 kg *Huperzia serrata* (Thunb.) Trev. in the extracting tank and put in 20 fold water solution containing 1.5% tartaric acid. Stir dynamically to abstract for 36 hours under the condition of 45° C.;

Concentrating: Concentrate the solution from permeation to 100 L;

Extracting: Adjust the pH value of the enriched solution to 9 with aqueous ammonia and extract with chloroform 4 times repetitively. Combine the chloroform extraction solution and concentrate to remove chloroform. concentrate to 100 L;

Back extraction with acid: Extract the above mentioned solution with 2% citric acid water solution 3 times repetitively;

Activated carbon decolorizing: Dilute the extraction solution of acid water 10 fold. The add-on of the activated carbon is 1% of the volume of the diluted solution. Stir 30 minutes and filter to get transparent solution;

Concentrating: Concentrate the above mentioned solution to 200 L;

Column chromatography: Load the above mentioned extractum onto the silicon gel column and elute gradiently with the eluent of methanol-chloroform. Collect the fractions of the eluent of methanol-chloroform (25:75);

Concentrate the above combined fractions to 500 ml and lyophilize in vacuum refrigeration machine to obtain 50g of the extract of *Huperzia serrata* (Thunb.) Trev. The yield of the extract was 0.05% by the herb, containing 32% HupA and 65% HupB.

EXAMPLE 4

Preparation Procedure IV:

Abstracting: pulverize 100 kg *Huperzia serrata* (Thunb.) Trev. in the extracting tank and put in 20 fold water solution containing 1.5% tartaric acid. Stir dynamically to abstract for 36 hours under the condition of 30° C. In the residues 10 fold 65% ethanol is added and abstract through reflux for 2 hours under the condition of 85° C.;

Concentrating: Concentrate the solution from permeation to 100 L;

Extracting: Adjust the pH value of the enriched solution to 9 with aqueous ammonia and extract with chloroform 4 times repetitively. Combine the chloroform extraction solution and concentrate to remove chloroform. Concentrate to 100 L;

Back extraction with acid: Extract the above mentioned solution with 2% citric acid water solution 3 times repetitively;

Activated carbon decolorizing: Dilute the extraction solution of acid water 10 fold. The add-on of the activated carbon is 1 % of the volume of the diluted solution. Stir 30 minutes and filtered to get transparent solution; and collect the fraction B of the eluent of methanol-chloroform (50:50);

Add 2 fold deionized water to the residues extract concentrate obtained in step 2, stir homogeneously and precipitated for 6 hours. Centrifuged the supernatants with high speed of 16000 r/min. Load the centrifugate onto the macroporous resin and elute gradiently with water, 20% ethanol and 65% ethanol successively. Collect the fraction of 65% ethanol.

Combined above (7)b fraction and (8) fraction and concentrate to 500 ml and lyophilize in vacuum refrigeration machine to obtain 150 g of the extract of *Huperzia serrata* (Thunb.) Trev. The yield of the extract was 0.15% by the herb, containing 10% HupA ,25% HupB and 25% total alkaloids.

EXAMPLE 5

Preparation of Tablet:

| Prescription (1000 tablets) | |
|---|---|
| Ingredients | Weight (g) |
| extract of *Huperzia serrata* (Thunb.) Trev. | 0.1 |
| | (HupA:HupB = 1:2) |
| Lactose | 9.7 |
| Corn starch | 20 |

-continued

| Prescription (1000 tablets) | |
| --- | --- |
| Ingredients | Weight (g) |
| Microcrystallic Cellulose | 5 |
| Calcium sulfate | 10 |
| Cross-linked carboxyl methyl cellulose | 5 |
| Magnesium stearate | 0.2 |
| Total | 50 |

According to the sequential steps for preparing the tablets, mixed the extract of *Huperzia serrata* (Thunb.) Trev. and other supplements homogenously by the mixing method of equivalent and progressive addition. Produced the granules by wet method and granulating after drying. Add magnesium stearate to mix homogeneously and pressed into 50 mg per tablet.

EXAMPLE 6

Preparation of Capsule:

| Prescription (1000 capsules) | |
| --- | --- |
| Ingredients | Weight (g) |
| extract of *Huperzia serrata* (Thunb.) Trev. | 0.1 (HupA:HupB = 1:2) |
| Corn starch | 30 |
| Dextrin | 29.3 |
| Magnesium stearate | 0.6 |
| Total | 60 |

According to the sequential steps of preparing the capsules, mixed the extract of *Huperzia serrata* (Thunb.) Trev. and other supplements such as corn starch and dextrin homogeneously by the mixing method of equivalent and progressive addition to make the granules with magnesium stearate as lubricant and choose No. 5 capsule. Filled with the medicine and sealed.

EXAMPLE 7

Preparation of Granule:

| Prescription (1000 bags) | |
| --- | --- |
| Ingredients | Weight (g) |
| extract of *Huperzia serrata* (Thunb.) Trev. | 0.1 (HupA:HupB = 1:2) |
| dextrin | 199.9 |
| Total | 200 |

According to the sequential steps of preparing the granules, sieved the extract of *Huperzia serrata* (Thunb.) Trev. and dextrin respectively and mixed them homogeneously. Prepared the soft material with ethanol-water, screened to make granule, dried and sieved to obtain the product.

EXAMPLE 8

Preparation of Nasal Fluid:

| Prescription (1000 bottles) | |
| --- | --- |
| Ingredients | Weight (g) |
| extract of *Huperzia serrata* (Thunb.) Trev. | 5 (HupA:HupB = 1:2) |
| 2,4-dimethyl-β-cyclodextrin | 244 |
| Sorbitol | 50 |
| sodium EDTA | 0.5 |
| benzalkonium chloride | 0.5 |
| Total | 250 |

The powder prepared as the above mentioned dosage was mixed with 5000 ml distilled water before using.

EXAMPLE 9

Preparation of Aerosol:

| Prescription (1000 bottles) | |
| --- | --- |
| Ingredients | Weight (g) |
| extract of *Huperzia serrata* (Thunb.) Trev. | 10 (HupA:HupB = 1:2) |
| ethanol | 540 |
| Vitamine C | 1 |
| F12 | Proper content |

According to the sequential steps of preparing the aerosol, dissolved the extract of *Huperzia serrata* (Thunb.) Trev. with ethanol and distilled water, mixed with projection agent to make a homogeneous solution.

EXAMPLE 10

Preparation of PAP Patcher:

| Prescription (1000 tablets) | |
| --- | --- |
| Ingredients | Weight (g) |
| extract of *Huperzia serrata* (Thunb.) Trev. | 0.5 (HupA:HupB = 1:2) |
| Polyacrylic ester | 18 |
| Laurocapram | 0.6 |
| Laurie acid | 1.8 |
| Propylene glycol | 5.4 |
| Ethyl acetate | 13.7 |
| Total | 40 |

According to the sequential steps of preparing the PAP Patcher, shake the extract of *Huperzia serrata* (Thunb.) Trev., skin transdermal enhancers and viscosity polymeric compound homogeneously. Coated it on polyester non-adherent layer, dried for 2 min under 60° C. and covered with polyurethane as backing film. Cut out the tablets.

EXAMPLE 11

Preparation of Powder for Injection:

| Prescription (1000 bottles) | |
| --- | --- |
| Ingredients | Weight (g) |
| extract of *Huperzia serrata* (Thunb.) Trev. | 0.05 |
| | (HupA:HupB = 1:2) |
| Hydrochloric acid | Proper content |
| Injection water | 1000 ml |

According to the sequential steps of preparing the powder-injection, the extract of *Huperzia serrata* (Thunb.) Trev. was dissolved with 10% hydrochloric acid solution prepared with injection water, adjusted to pH 4.0-5.5 and ultrafiltered to degerm with millipore filter membrane. Then it was filled in the bottles according to the dosage and lyophilized in the refrigeration machine. The bottles was covered with plug.

The main drug effect and toxicological experiments of the *Huperzia serrata* (Thunb.) Trev. composition of the invention were listed as following:

Experiment 1

Main Drug Effect Study

1. Experimental Samples:

Composition 1: the extract of *Huperzia serrata* (Thunb.) Trev. obtained in Example 1, white, 66% HupA and 33% HupB and the weight ratio of them is 2:1;

Composition 2: the extract of *Huperzia serrata* (Thunb.) Trev., white, 49% HupA and 49% HupB, and the weight ratio of them was 1:1;

Composition 3: the extract of *Huperzia serrata* (Thunb.) Trev. obtained in Example 3, white, 32% HupA and 65% HupB, and the weight ratio of them was 1:2;

Control medicine: HupA, white powdered crystal, formula $C_{15}H_{18}N_2O$, molecular weight 242.32, mp229-230° C.;

2. experimental animals: SD rats, male, body weight 250-300 g.

3. experimental steps: Add 1 ml of phosphate buffer (pH=7.2) and heparin-added anticoagulant whole blood of rat in a test tube. Preheat for 5 min on water bath of 37° C. Add 1 ml acetylcholine solution, 0.007 mol/L in the test tubes according to the number sequence of the samples quickly and correctly. After reacting for 30 min in the water bath of 37° C., add 4 ml alkaline azanol according to the same number sequence in the test tubes and shake thoroughly for 2 min. Continue to add 2.0 ml hydrochloric acid solution of 1:2, after shake thoroughly for 2 min, add 2.0 ml 10% iron tri-chloride solution and shake thoroughly. Filter the 10 ml above mentioned solution with ordinary filter paper and add the elusion The protein was discarded in a cuvette to colorimetrically determined at the wave length of 530 nm. The effect of the inhibition of ChE activity was controlled by the enzyme activity (100%) wherein the inhibitor was not added. Plot with the percentage of the residual enzyme activity to the negative logarithm (pI) of the concentration (g/l) of the experimental samples. According to the plot, the value of $pI_{50}$, that was, the dosage of the medicine which inhibited 50% of the enzyme activity was obtained.

4. Experimental results: Plot by the C of ChE activity of the rat's whole blood to the negative logarithm (pI) of the concentration (g/l) of the experimental samples. Figure of the apparent inhibition strength of ChE activity of Compositions 1, 2 and 3 was obtained. The value of $IC_{50}$ (g/l) of inhibiting 50% of ChE activity, see Table 1.

TABLE 1

Assay of $IC_{50}$ of ChE activity of the extract of *Huperzia serrata* (Thunb.) Trev. containing different ratios of HupA and HupB

| Experimental samples | Ratio of the components HupA:HupB | $IC_{50}$ g/l |
| --- | --- | --- |
| Composition 1 | 2:1 | $8.04 \times 10^{-6}$ |
| Composition 2 | 1:1 | $8.40 \times 10^{-6}$ |
| Composition 3 | 1:2 | $9.74 \times 10^{-6}$ |
| Control medicine | 1:0 | $4.82 \times 10^{-6}$ |

The result showed that all of the extracts of *Huperzia serrata* (Thunb.) Trev. with different ratios of HupA and HupB all had apparent inhibitory effect on the enzyme activity of cholinesterase in the in vitro whole blood.

Experiment 2

Acute Toxicity Test

1. Experimental Samples:

the same in Experiment 1

2. experimental animals: ICR mice, SPF, male and female, body weight 18-20 g, all bought from Shanghai SIPPR/BK Experimental Animal Co. Laboratory animal license No. SCXK (Hu)2003-0002

3. experimental conditions: SPF experimental environment. Grouped the experimental mice 5 per cage and bred. The breeding temperature was 22±2° C., the humidity was 60-70% and Laboratory animal license number was SCXK (Hu)2002-0035. The mice were bred with the solid high pressure forage. Fasted 12 hours before the test but no water-deprivation.

4. experimental steps: After fasting 12 hours, 280 male SPF mice were drenched through stomach directly with Compositions 1, 2, 3 and the control medicine respectively. After administration, the mice were liberated to diet. Observed the mice once immediately, every morning and every afternoon for 7 continuous days. The mice were observed once a day from the $8^{th}$ day. Record the mortality and toxic reaction of the experimental animals.

5. experimental results: By Calculating using simplified probit method, $LD_{50}$ (confidence limit 95%) of Compositions 1, 2, and 3 were 9.23±1.9, 13.76±3.0, and 20.33±4.29 mg/kg respectively. The time of death of the toxified animals was between 9 min and 12 hours. The main toxic symptoms were salivation, lacrimation, twitching, convulsion, hidrorrhea, asphyxia and death. see Table 2.

TABLE 2

Acute toxicity test of the extract of *Huperzia serrata* (Thunb.) Trev. containing different ratios of HupA and HupB (HupA:HupB were 2:1, 1:1, and 1:2)

| Experimental samples | Ratio of the components HupA:HupB | $LD_{50}$ mg/kg |
| --- | --- | --- |
| Composition 1 | 2:1 | 9.23 ± 1.9 |
| Composition 2 | 1:1 | 13.76 ± 3.0** |
| Composition 3 | 1:2 | 20.33 ± 4.29** |
| Control medicine | 1:0 | 6.03 ± 1.46** |

*P < 0.05,
**P < 0.01, compared with the control medicine

The result showed that $LD_{50}$ (confidence limit 95%) of the extract of *Huperzia serrata* (Thunb.) Trev. containing the HupA and HupB with the ratios as 2:1, 1:1, and 1:2 respectively are 9.23±1.9, 13.76±3.0, and 20.33±4.29 mg/kg respectively, in which the toxicity of the extract of *Huperzia serrata* (Thunb.) Trev. comprising the HupA and HupB with the ratios 1:1 and 1:2 respectively fell apparently comparing with that of HupA. The decrease was 128% and 237% respectively.

Discussions

1. Comparing with the control (only containing HupA), both $LD_{50}$ and $IC_{50}$ values of the compositions containing different ratios of HupB increased apparently. The increasing rate of $LD_{50}$ of Compositions 1, 2, and 3 were 53%, 128%, and 237%. The increasing rates of $IC_{50}$ of Compositions 1, 2, and 3 were 67%, 74%, and 102%. See Table 3.

TABLE 3

The relationship between the ratios of HupB in the compositions and the values of $LD_{50}$ and $IC_{50}$

| Experimental samples | Ratio of the components HupA:HupB | $LD_{50}$ mg/kg | %* | $IC_{50}$ $10^{-6}$ g/l | %** |
|---|---|---|---|---|---|
| Composition 1 | 2:1 | 9.23 | 53 | 8.04 | 67 |
| Composition 2 | 1:1 | 13.76 | 128 | 8.4 | 74 |
| Composition 3 | 1:2 | 20.33 | 237 | 9.74 | 102 |
| Control medicine | 1:0 | 6.03 | | 4.82 | |

*$LD_{50}$ % = ($LD_{50}$ of the composition – $LD_{50}$ of the control medicine)/$LD_{50}$ of the control medicine
**$IC_{50}$ % = ($IC_{50}$ of the composition – $IC_{50}$ of the control medicine)/$IC_{50}$ of the control medicine The results in Table 3 showed that the increasing degree of $LD_{50}$% is apparently higher than that of $IC_{50}$% when the ratio of HupB in the experimental samples increases. When the ratio of HupA and HupB was 1:2, $LD_{50}$%/$IC_{50}$%>2. The result showed when the value of HupB/HupA was more than 0.5 in the composition, the value of $LD_{50}$%/$IC_{50}$% increased gradually when the ratio of HupB increased. The clinical significance is that the safety of the composition will be substantially improved when it contains certain amount of HupB.

2. The value of $LD_{50}$ of Compositions 1, 2 and 3, wherein the contents of HupA were 6.15, 6.88, and 6.78 mg/kg, the contents of HupB were 3.08, 6.88, and 13.55 mg/kg, respectively. Comparing with the control medicine (pure HupA), the contents of HupA increased 2.0%, 14.1%, and 12.4% in turn. See Table 4.

TABLE 4

The relationship between the change in content of HupA, HupB in the compositions and the values of $LD_{50}$

| Experimental samples | Ratio of the components HupA:HupB | composition mg/kg | HupA mg/kg | %* | HupB mg/kg |
|---|---|---|---|---|---|
| Composition 1 | 2:1 | 9.23 ± 1.9 | 6.15 | 2.0 | 3.08 |
| Composition 2 | 1:1 | 13.76 ± 3.0** | 6.88 | 14.1 | 6.88 |
| Composition 3 | 1:2 | 20.33 ± 4.29** | 6.78 | 12.4 | 13.55 |
| Control medicine | 1:0 | 6.03 ± 1.46** | 6.03 | | 0 |

*P < 0.05,
**P < 0.01, compared with the control medicine

Correspondingly, the values of $IC_{50}$ of Composition 1, 2 and 3, wherein when the contents of HupA were 5.36, 4.02, and $3.25 \times 10^{-6}$ g/l respectively, the contents of HupB were 2.68, 4.38, and $6.49 \times 10^{-6}$ g/l respectively. Comparing with the control (pure HupA), the contents HupA increases 11.2, −16.6, and −32.6%. See Table 5.

TABLE 5

The change relationship between the values of $IC_{50}$ and the content of HupA, HupB in the compositions

| Experimental samples | Ratio of the components HupA:HupB | composition $10^{-6}$ g/l | HupA $10^{-6}$ g/l | %* | HupB $10^{-6}$ g/l |
|---|---|---|---|---|---|
| Composition 1 | 2:1 | 8.04 | 5.36 | 11.2 | 2.68 |
| Composition 2 | 1:1 | 8.40 | 4.02 | −16.6 | 4.38 |
| Composition 3 | 1:2 | 9.74 | 3.25 | −32.6 | 6.49 |
| Control medicine | 1:0 | 4.82 | 4.82 | | 0 |

It was shown in Table 4, comparing with that of the control medicine, the value of $LD_{50}$ of Compositions 1, 2, and 3 increased greatly. Although the main cause of this was that the ratios and absolute content of HupB increased greatly, it is also because the content of HupA increased obviously. The absolute contents of HupA increased 2.0, 14.1, and 12.4% in turn. The result showed that when HupB/HupA≥0.5 in the composition, the value of $LD_{50}$% would increase along with the increase of the ratio of HupB, and meanwhile the absolute content of HupA increased accordingly. It implied that the safety of the composition will be substantially improved when it contains certain amount of HupB.

It was shown in Table 5, the ratio and absolute content of HupB of Compositions 1, 2, and 3 increases in turn, and the ratio and absolute content of HupA decreased in Compositions 2, and 3 in turn, and decrease ratios of the later were 16.6 and 32.6%. Comparing with the control medicine, the change of the ratio of HupA and HupB and their absolute value had little affect on the value of $IC_{50}$. The results showed that when the value of HupB/HupA≥1 in the composition, the activity of HupA increased along with the increase of the ratio of HupB. That is to say, although the absolute content of HupA decreased, because of the increase in the ratio of HupB, the activity and the drug effect of the composition could be equal to that of the control medicine (the absolute content of HupA is relatively higher). It implied that the therapeutic effect of the composition will be substantially improved when it contains certain amount of HupB.

The extract of *Huperzia serrata* (Thunb.) Trev. of the invention (mainly characterized in the decided ratio of HupA and HupB in the compositions) have apparent effect on inhibiting the activity of cholinesterase, and are safer than HupA apparently. The results of the main study of the drug effect and the acute toxicity test provided a solid basis for the use thereof in clinically improving memory function in child, ameliorating dysmnesia in adult, preventing and curing AD and cognition dysfunction.

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A *Huperzia serrata* (Thunb.) Trev. composition for treating a memory and/or cognition dysfunction, comprising a combination of isolated fractions of an extract of *Huperzia serrata* (Thunb.) Trev., wherein the composition contains 30-99 wt % of total alkaloids, the total alkaloids contain Huperzine A and Huperzine B, the total content of the Huperzine A and Huperzine B is 50-99 wt % of total alkaloids; and the weight ratio of the Huperzine A and Huperzine B is 1:0.5-5; wherein the composition is obtained by the following steps (a)-(c):

a) extracting a raw material of *Huperzia serrata* (Thunb.) Trev with an acid aqueous solution having a pH between 1-3, thereby obtaining an extract solution of the raw material, and extracting a residue of the extraction of the raw material with an aqueous solution, thereby obtaining an extract solution of the residue;

b) concentrating the extract solution of the raw material and the extract solution of the residue obtained in step a), thereby obtaining a concentrate of the extract solution of the raw material and a concentrate of the extract solution of the residue, and treating the concentrates as follows:

(b1) extracting, concentrating, decolorizing and re-concentrating the concentrate of the extract solution of the raw material, thereby obtaining a reconcentrate of the concentrate of the extract solution of the raw material; loading the reconcentrate onto a first chromatography column and eluting the first chromatography column with water, a C1-C6 alkanol solvent, or a mixture including water and the C1-C6 alkanol solvent, and collecting a fraction b1 containing the total alkaloids;

(b2) diluting and centrifuging the concentrate of the extract solution of the residue, loading a supernatant obtained from the centrifuging onto a second chromatography column and eluting the second chromatography column with water, a polar solvent, a non-polar solvent, or a mixture including water, the polar solvent and the non-polar solvent, and collecting a fraction b2 containing total alkaloids; and c) combining fractions b1 and b2 and concentrating and drying the combined fractions b1 and b2, thereby obtaining the *Huperzia serrata* (Thunb.) Trev. composition.

2. The *Huperzia serrata* (Thunb.) Trev. composition of claim 1 further comprising one or more of Huperzine C, Huperzine D, Huperzine E, Huperzine F, Huperzine G, 6-β-hydroxyhuperzine A, Huperzinine, Lycodoline, Lycodavine, Serratinine, Serratine, 8-Deoxyserratinine, and Phlegmariurine N.

3. The *Huperzia serrata* (Thunb.) Trev. composition of claim 1, further comprising one or more of Galangin, Kaempferol, Quercetin, Apigenin, Genkwanin, Luteolin, Vitexin, Serratenediol, Serratriol, Tohogenol, and 21-epi-Serratenediol, wherein the content of one or more of Galangin, Kaempferol, Quercetin, Apigenin, Genkwanin, Luteolin, Vitexin, Serratenediol, Serratriol, Tohogenol, and 21-epi-Serratenediol is 1-50 wt % of the total weight of the composition.

4. The *Huperzia serrata* (Thunb.) Trev. composition of claim 1, wherein the acid aqueous solution in step (a) is at least one selected from the group consisting of hydrochloric acid, tartaric acid and citric acid, and the aqueous solution is used to extract the residue in step (a), the aqueous solution contains an alcohol that is at least one selected from the group consisting of methanol and ethanol.

5. The *Huperzia serrata* (Thunb.) Trev. composition of claim 1, wherein the C1-C6 alkanol solvent in step (b1) is at least one selected from the group consisting of methanol, ethanol, n-butanol, C-4 alkanol, and C-5 alkanol, or a mixture thereof with water of any proportion, and the non-polar solvent in step (b2) is at least one selected from the group consisting of methanol and ethanol.

6. The *Huperzia serrata* (Thunb.) Trev. composition of claim 1, wherein each of the first and second chromatography columns used in steps (b1) and (b2) is a silica gel column, or includes a macroporous resin, a cation exchange resin or a polyamide resin, and an eluting solution used in the first and second chromatography columns is at least one selected from the group consisting of C1-C3 alkanol solvent, acetone, chloroform, methyl ester and ethyl ester of C1-C3 alkanol.

7. The *Huperzia serrata* (Thunb.) Trev. composition of claim 1, wherein the extract of *Huperzia serrata* (Thunb.) Trev. composition is obtained by the steps consisting essentially of (a)-(c).

* * * * *